United States Patent
Ballini

[19]

[11] Patent Number: 6,135,358
[45] Date of Patent: Oct. 24, 2000

[54] APPARATUS FOR WASHING THE NASAL CAVITIES

[75] Inventor: Fausto Ballini, Bovezzo, Italy

[73] Assignee: Mefar S.p.A., Bovezzo, Italy

[21] Appl. No.: 09/174,567

[22] Filed: Oct. 16, 1998

[30] Foreign Application Priority Data

Oct. 17, 1997 [IT] Italy ................................. MI97A2348

[51] Int. Cl.⁷ ....................................................... B05B 7/30

[52] U.S. Cl. ........................................... 239/121; 239/348

[58] Field of Search .................................... 239/112, 113, 239/346, 347, 348, 8, 318, 327, 120–122; 222/212, 215

[56] References Cited

U.S. PATENT DOCUMENTS

| 1,822,743 | 9/1931 | Mitchell | 239/348 |
| 2,744,663 | 5/1956 | White | 222/215 X |
| 4,568,004 | 2/1986 | Goncalves | 222/212 X |
| 4,940,185 | 7/1990 | Fu | 239/347 X |
| 5,328,061 | 7/1994 | Libit et al. | 222/212 |
| 5,655,686 | 8/1997 | Jermyn | 222/422 X |

*Primary Examiner*—Kevin Weldon
*Attorney, Agent, or Firm*—Herbert Dubno

[57] ABSTRACT

A nasal atomized shower apparatus has a body defining an atomizing chamber, a pressurized air injector arranged at the region of feed of washing liquid to be atomized and facing the atomizing chamber and a conduit for discharging the washing liquid. The apparatus further includes a valve associated with the body, and adapted to control the pressure of the pressurized air for releasing the excessive pressure.

13 Claims, 4 Drawing Sheets

APPARATUS FOR WASHING THE NASAL CAVITIES

BACKGROUND OF THE INVENTION

1. Field of the Invention

The present invention relates to an apparatus for washing the nasal cavities and related areas, such as the paranasal sinuses, nasopharynx, pharynx, eustachian tube, and middle ear.

2. Description of the Prior Art

Several apparatuses for washing the nasal cavities and related areas are known on the market and used effectively. Conventional apparatuses comprise a body formed by a first member having a nozzle and a second member formed as a bell and defining an atomizing chamber. A different type of apparatus comprises a further member defining a collection chamber adapted to collect the discharge material containing catarrh from the nasal cavities.

Each of the conventional apparatuses may only be used with the specifically provided aerosol device adapted to ensure a constant atomizing pressure and preventing possible overpressures.

Furthermore, the user must turn the apparatus on only after having applied the container to the nose in order to avoid getting the face wet with the aerosol spray.

3. Objects of the Invention

An object of the present invention is to eliminate the above mentioned problems by providing an apparatus for washing the nasal cavities which can be used with any aerosol equipment.

A further object is to provide an apparatus adapted to produce aqueous micelles even after turning the aerosol device on.

A further object is to provide an apparatus adapted to produce a jet of aqueous micelles having a diameter greater than 20 microns to further enhance the cleaning action on the nasal cavities and surrounding regions.

A further object of the invention is to provide an apparatus than can be used by users of any age and with different conditions, by simply replacing the bell member to be introduced in the nose.

Still a further object of the invention is to provide a safe and reliable apparatus also having a versatile use.

SUMMARY OF THE INVENTION

The above objects, and other aims that will become apparent to those skilled in the art, are achieved by an apparatus for washing the nasal cavities comprising a body defining at least one atomizing chamber, at least one pressurized air injector arranged at the region of feed of washing liquid to be atomized and facing said atomizing chamber and discharge means for discharging at least said washing liquid, said apparatus further comprising valve means associated with said body, and adapted to control the pressure of said pressurized air for releasing the excessive pressure.

Further characteristics and advantages of the invention will become apparent from a reading of the detailed description of a preferred but not exclusive embodiment of the apparatus according to the invention, illustrated only by way of a non-limiting example in the accompanying drawings.

BRIEF DESCRIPTION OF THE DRAWING

The above and other objects, features, and advantages will become more readily apparent from the following description, reference being made to the accompanying drawing in which.

DESCRIPTION OF THE PREFERRED EMBODIMENTS OF THE INVENTION

Figure 1:
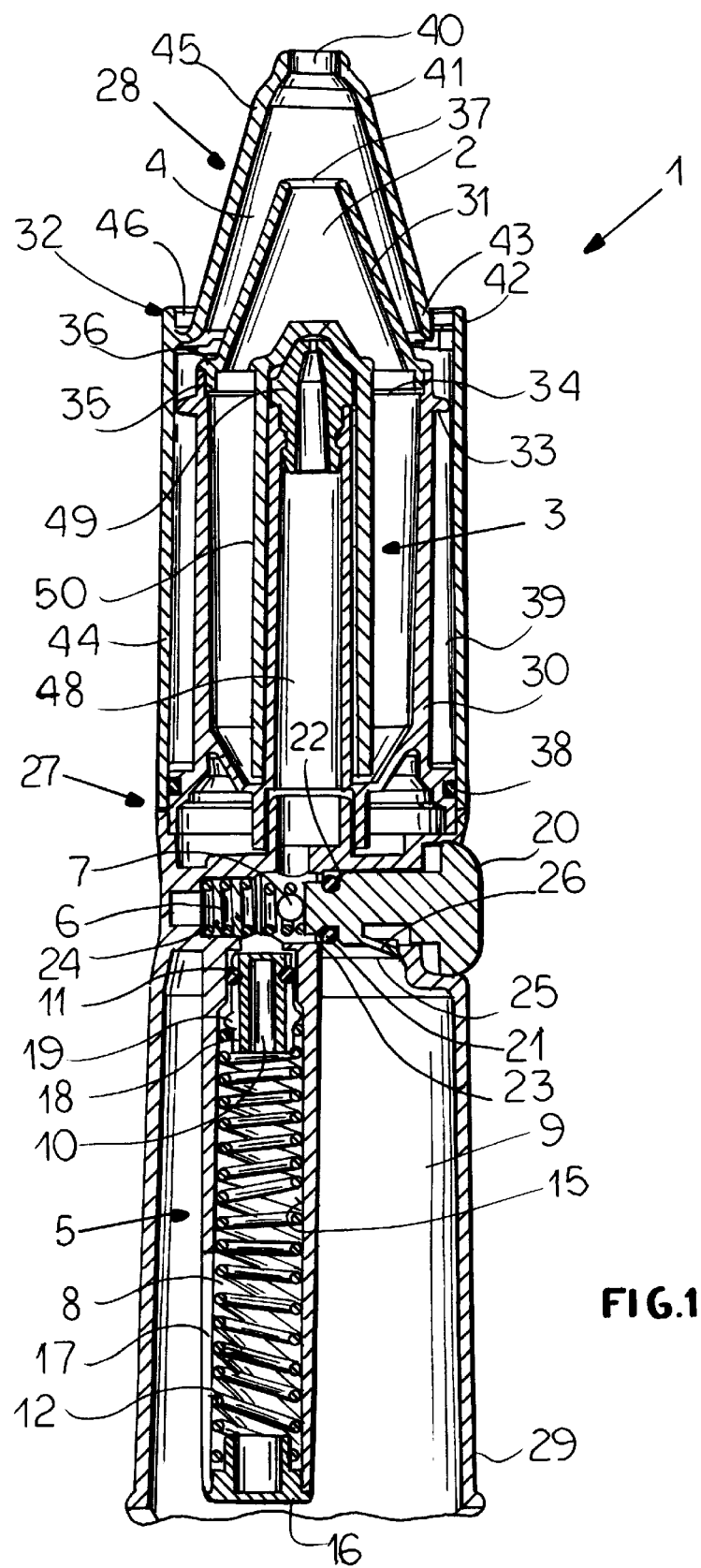
FIG. 1 is a front elevational sectional view of the apparatus according to the invention shown with the push-button undepressed.
Figure 2:
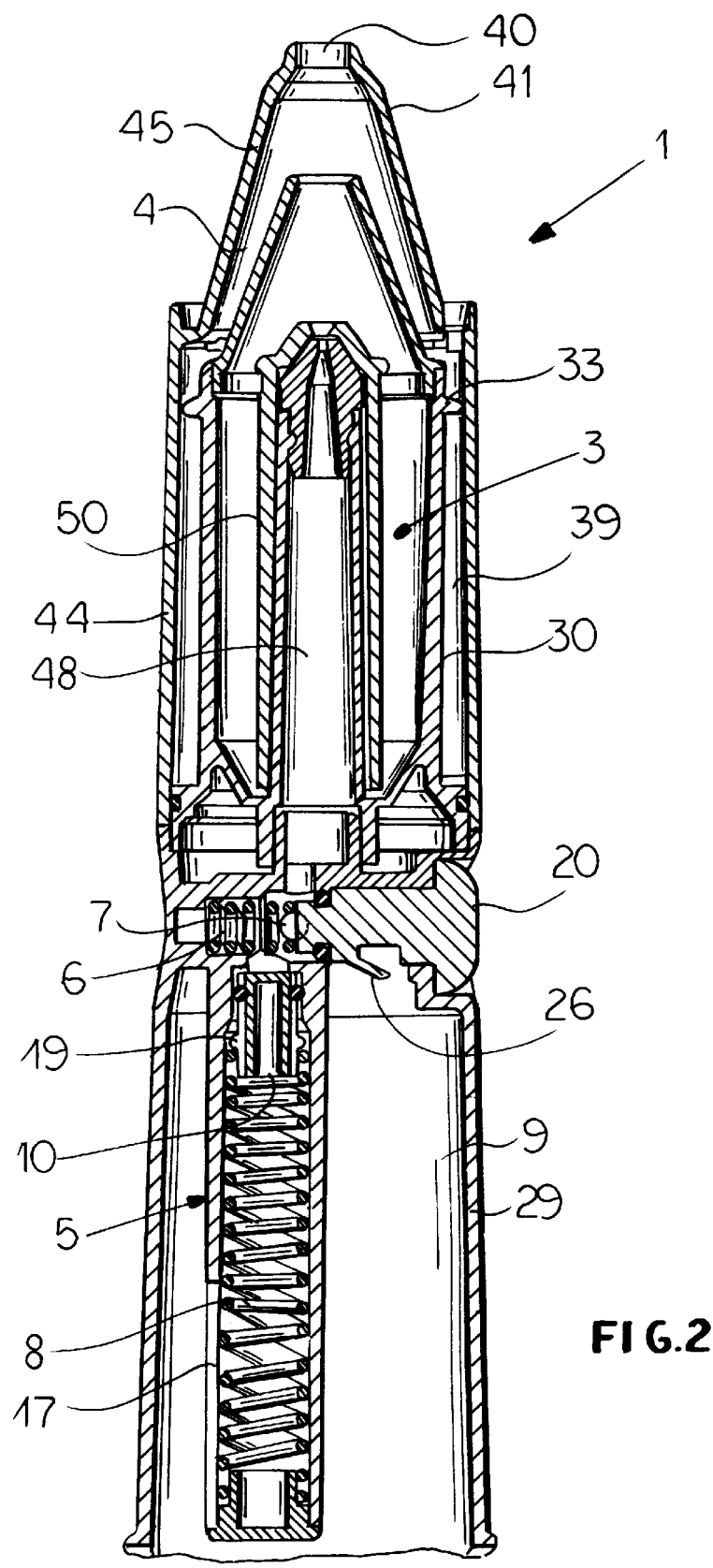
FIG. 2 is a front elevational sectional view of the apparatus according to the invention shown with the push-button depressed.
Figure 3:
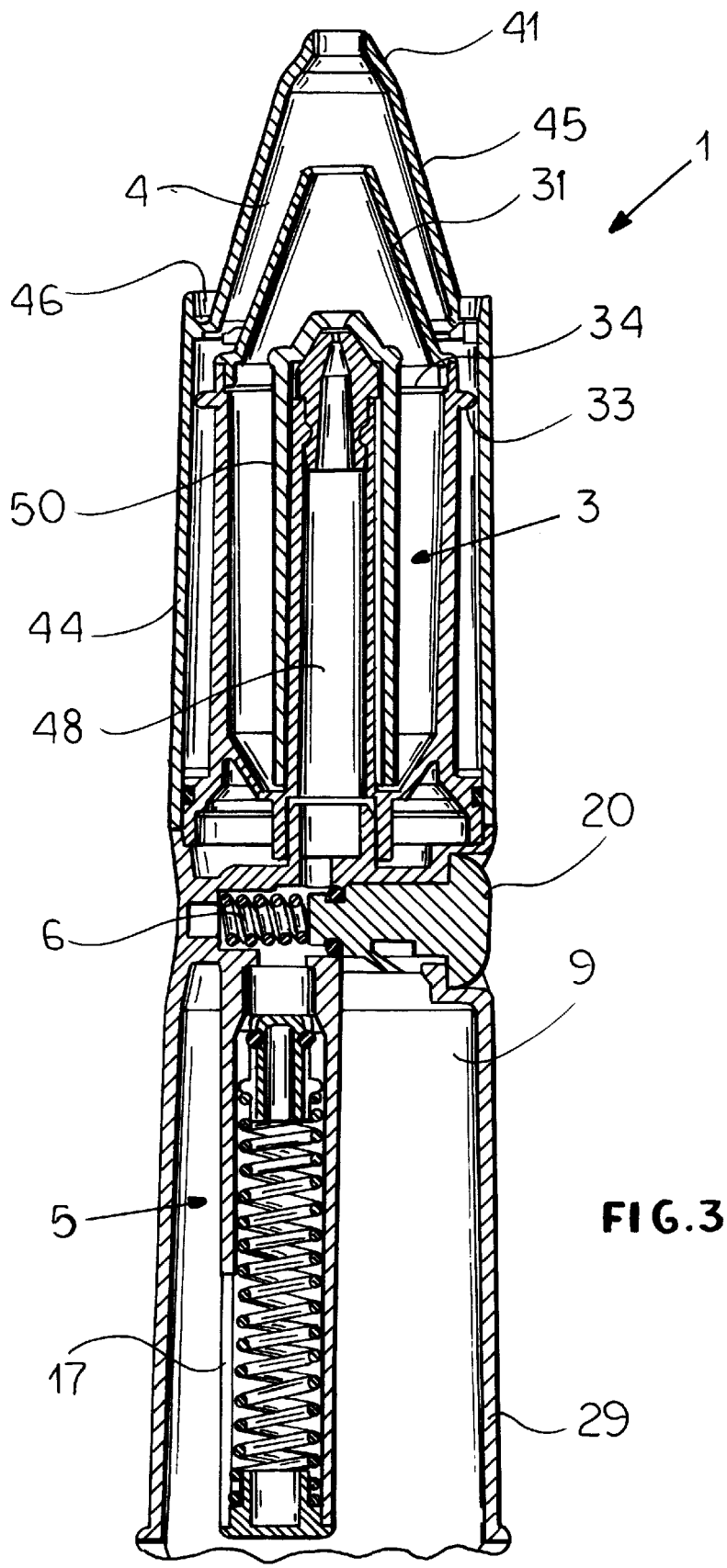
FIG. 3 is a front elevational sectional view of the apparatus according to the invention shown with the conduit 8 partially opened by the slider 10.
Figure 4:
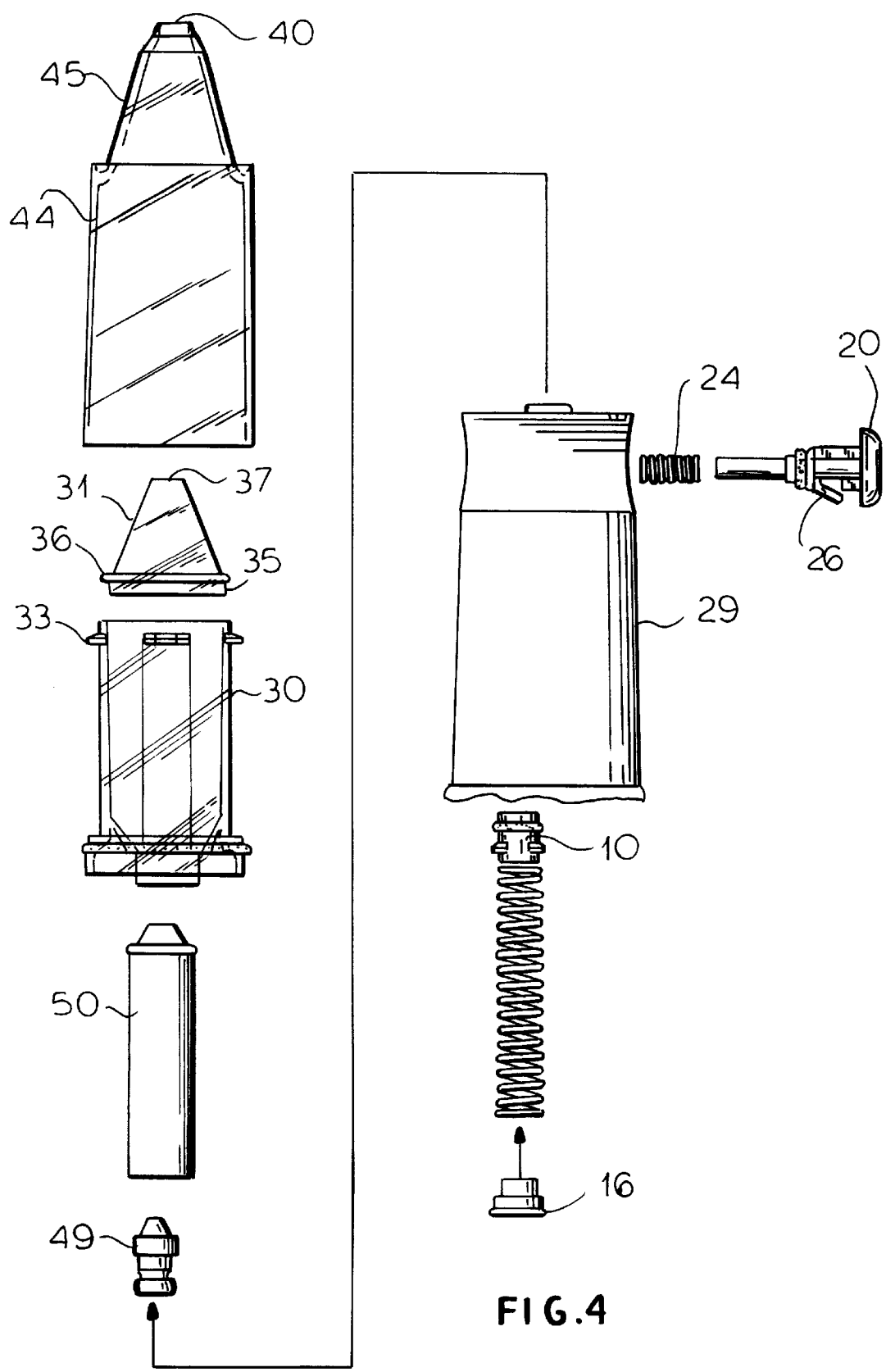
FIG. 4 is an exploded view of the main component parts of the apparatus.

The apparatus according to the invention, generally designated by the reference numeral 1, is constituted by a body comprising an atomizing chamber 2, an injector 3, discharge means 4 for discharging the washing liquid and pressure control means 5.

A chamber 6 inside the body receives pressurized air from a port 7. The chamber 6 is connected to the injector 3, with a first conduit 8 and with a second conduit 9 for discharging the pressurized air for controlling the pressure and for controlling the start of the atomizing action.

The pressure control means comprises a slide 10, having a seal means 11, and adapted to move inside conduit 8. Slide 10 is biased by first elastic means, namely a calibrated helicoidal spring 12. Conduit 8 has a region 13, that can be engaged by slide 10 to ensure a seal, a region 14 with a suitably variable diameter for discharging pressurized air and connected with a region 15 having a conduit diameter greater than the diameter of slide 10. The end of slide 10 has a cylindrical shape with four ridges 18 interrupted by a seat for a first seal means, namely an O-ring 11. A first end of spring 12 engages four teeth 19 provided on the ridges 18 while the second end of spring 12 is in contact with a cover 16. An atomizing start up means is arranged inside the chamber 6, namely a control member constituted by a push button 20, which is biased by second elastic means, namely an helicoidal spring 24, and the second seal means constituted by a seal or gasket 21 arranged in an adapted seat 22 formed on the body of push-button 20. Push-button 20 also has a protruding finger member 26 coupled to a slit 25 for guiding the push-button and for keeping it in place by abutting on the body of the apparatus.

Chamber 6 has a discharge valve means constituted by an opening 23 which makes chamber 6 communicate with the outside through the seat of push-button 20, slit 25 and conduit 9. Push-button 20 extends inside the opening 23 and partially engages its section also in the rest position.

The body of apparatus 1 comprises a first portion, operating as a hand grip 27 and substantially cylindrically shaped, wherein the push button 20 is arranged. The body also comprises a second portion constituted by two coaxial bell members 28, one of the bell members being adapted to be inserted in the nostrils. The cylindrical hand grip 27 of the apparatus is constituted by two sealingly joined members 29 and 30. Control means 20 and 23 and pressure control means 5 are arranged in the first or base member 29, while injector 3 is arranged in the second or tubular member 30 and has shaped surfaces adapted to enable the bell members 28 to couple. A cavity or interspace 4 is provided between the bell members 31 and 32 and its size may be varied by changing the bell members in order to obtain a large or narrow cavity or no cavity at all when the bell members walls are in contact. The second member 30 has spacer members 33 arranged along a circumference at the connection region of the bell 31.

These spacer members are constituted by projections on the second or tubular member 30 and adapted to support the bell member 32.

The first bell member 31 has a substantially truncated cone shape having a base 34, with an edge 35 for coupling to the tublar member 30, and an edge 36 abutting the half member 30. An opposite end of the bell 31 has an outlet 37 for the liquid micelle jet. According to a further aspect of the invention, such outlet 37 extends also on the side surface of member 31, for example in the form of longitudinal slit.

The outer bell member 32 has a first cylindrical region 44 one end thereof being adapted to surround the tubular member 30 forming a discharged washing liquid collect chamber 39. The seal of said collect chamber 39 is provided by seals or gaskets 38 arranged in a seat formed in the tubular member 30. A second region of member 32 has a truncated cone shape 45 having an end provided with a tapered region 41, having a decidedly reduced diameter, followed by the micelle jet outlet 40. The region of union of parts 44 and 45 of member 32 has a channel 46 formed by the wall of the truncated cone 45 and by an edge 42 extending from the cylindrical region 44. Any possible oscillation of the cylindrical region 44 is prevented by projections 33. Channel 46 has apertures 43 connecting the collect chamber 39 with the outside for allowing to the washing liquid possibly present outside wall 45 of member 32 to be collected. For the same reason, bell 45 has planar regions on its surface (not illustrated in the drawings) angled towards said apertures 43 to promote the discharge of soiled liquid.

At least the bell members 31 and 32 and the injector are coaxial while the axis of conduit 8 is offset with respect to such members and injector.

Injector 3 is constituted by a conduit 48 associated with the tubular half member 30 and a first end of the conduit opens toward chamber 6. A second end of conduit 48 has a nozzle 49 for ejecting pressurized air. A cover 50 is provided above the conduit 48 and nozzle 49 and has a slightly greater diameter than the diameter of conduit 48 allowing to draw liquid by virtue of the venturi effect.

The operation of the apparatus according to the invention is apparent from what has been described and illustrated. With particular reference to the figures, considering the situation where the push-button 20 is not depressed, pressurized air enters hole 7 in chamber 6 and is therefrom partially discharged to the outside through opening 23, slit and conduit 9 and partially sent to the injector 3. In this situation, the air cannot prime the venturi effect: the air at the exit of the injector has no micelles of washing liquid.

Considering the situation where the push-button 20 is depressed, air enters chamber 6 through opening 7 and therefrom goes to the injector because the passage through opening 23 is blocked by the push-button 20. The air exiting the injector nozzle is in this case capable to prime a venturi effect and therefore a jet of micelles of washing liquid exits the apparatus.

In case the pressure in chamber 6 is greater than it should be, when the push-button is closed, the pressure control means 5 is activated and particularly the slide 10 compresses the calibrated spring 12 which opens conduit 8 and allows pressure which exceeds the calibration of the spring to be released.

The collection of washing liquid, exiting the nose and entering the apparatus, in chamber 39, is obtained by letting the liquid pass in the cavity 4 connected to chamber 39, and letting the liquid dripping along the external wall of the external bell 44, pass through the apertures 43 comprised in the collection region 46.

It has been seen in practice how the apparatus according to the invention is particularly advantageous as it can be used regardless of the type of pressurized air delivery device. Furthermore, the apparatus has improved properties of nasal cavities washing and of collection of the soiled liquid. Further advantages of the invention regard the possibility for the use to activate the atomizing action and to adapt the apparatus to his or her requirements by substituting one or more of the bell members.

The apparatus according to the invention is susceptible to numerous modifications and variations, all of which are within the scope of the inventive concept. All the details may furthermore be replaced with other technically equivalent elements.

In practice, the materials employed, as well as the dimensions, may be any according to the requirements.

What is claimed is:

1. An apparatus for washing a nasal cavity comprising a body defining at least one atomizing chamber, at least one pressurized air infector arranged at a region of feed of washing liquid to be atomized and facing said atomizing chamber and discharge means for discharging at least said washing liquid, valve means associated with said body, and adapted to control the pressure of said pressurized air for releasing the excessive pressure, said valve means being adapted to regulate said pressure of said atomizing air continuously, said body comprising at least a first portion having an ergonomical shape and adapted to allow to be gripped by a hand, and at least a member substantially shaped as a bell associated with said first portion and with other bell-shaped members having different shapes.

2. The apparatus, according to claim 1, wherein the outlet of micelles of liquid of said at least first bell-shaped member has a supplementary exit region extending on the side surface of said bell-shaped member.

3. The apparatus, according to claim 1, wherein said second bell-shaped member has at least a first portion having a cylindrical shape and at least a second portion having a truncated cone shape.

4. The apparatus, according to claim 1, wherein said second bell-shaped member has a projecting edge at the region joining said at least first portion to said substantially truncated cone second portion, said projecting edge extending at said substantially bell-shaped portion.

5. The apparatus, according to claim 1, wherein said injector and said valve means conduit have substantially parallel axes.

6. The apparatus, according to claim 1, wherein said injector and at least one of said bell-shaped members are substantially coaxial.

7. An apparatus for washing a nasal cavity comprising a body defining at least one atomizing chamber, at least one pressurized air injector arranged at a region of feed of washing liquid to be atomized and facing said atomizing chamber and discharge means for discharging at least said washing liquid, valve means associated with said body, and adapted to control the pressure of said pressurized air for releasing the excessive pressure, said valve means being adapted to regulate said pressure of said atomizing air continuously, a controlled prime means for priming the atomizing of said washing liquid when pressurized air is fed to said body, said controlled prime means comprising at least one control member having second seal means adapted to intercept said pressurized air, said first portion has sealingly associated base and tubular members, said base member accommodating said control tubular member accommodating said bell-shaped members.

8. The apparatus, according to claim 7, wherein said tubular member has spacer members between said tubular member and said at least second bell-shaped member.

9. The apparatus, according to claim 8, wherein said spacer members are constituted by projections arranged along at least one curved surface of said second member.

10. The apparatus, according to claim 7, wherein second bell-shaped member has slits connecting the outside with a cavity defined between said first and second bell-shaped members.

11. The apparatus, according to claim 7, wherein said first bell-shaped member has an abutment edge at a joining region with said tubular member, said abutment edge at least partially projecting from the surface of said tubular member coupled thereto.

12. The apparatus, according to claim 7, wherein said first half member comprises at least one chamber connected to said injector and to said pressure control valve means conduit, said chamber having at least one inlet for pressurized air.

13. A nasal irrigator comprising:

an outer bell member of ergonomic shape for holding in a hand of a user and formed at one end with a tapered region having an outlet for a micelle jet;

an inner bell member surrounded by said outer bell member and having a tubular region and a tapered region coaxial with said outer bell member, said tapered region having an outlet for said micelle jet spaced inwardly from and aligned with said outlet of the tapered region of said outer bell member;

an injector coaxially received in said inner bell member and having a nozzle aligned with said outlets for directing said micelle jet through said outlets;

a pushbutton valve assembly having a chamber communicating with a source of compressed air and with said injector for pressurization of said chamber upon actuation of said pushbutton valve assembly;

a tubular base member formed with said valve assembly and connected to said inner and outer bell members and receiving said assembly, said pushbutton valve assembly venting compressed air to said base member in an absence of actuation thereof; and a pressure controller in said base member communicating with said chamber for maintaining pressure in said chamber substantially constant upon actuation of the pushbutton valve assembly.

* * * * *